United States Patent

Walte et al.

[11] Patent Number: 5,979,221
[45] Date of Patent: Nov. 9, 1999

[54] METHOD FOR SEPARATING SELECTED MATERIALS IN A GAS CHROMATOGRAPH AND GAS CHROMATOGRAPH FOR CARRYING OUT THE METHOD

[75] Inventors: Andreas Walte; Wolf Münchmeyer, both of Schwerin; Gerhard Matz, Buchholz; Alexander Harder, Hamburg; Oliver Räther, Bremen, all of Germany

[73] Assignee: WMA Airsense Analysentechnik GmbH, Schwerin, Germany

[21] Appl. No.: 09/028,215

[22] Filed: Feb. 23, 1998

[30] Foreign Application Priority Data

Feb. 22, 1997 [DE] Germany .............................. 197 07 114

[51] Int. Cl.$^6$ ..................................................... G01N 30/54
[52] U.S. Cl. ............................. 73/23.25; 73/23.35; 95/87
[58] Field of Search ................................ 73/23.39, 23.35, 73/23.25, 23.26; 95/87; 96/103

[56] References Cited

U.S. PATENT DOCUMENTS

| 3,422,603 | 1/1969 | Redmond, Jr. . |
| 5,634,961 | 6/1997 | Gordon ......................................... 95/17 |
| 5,653,885 | 8/1997 | Jameson et al. ......................... 210/634 |
| 5,807,426 | 9/1998 | Ohtsuki et al. ............................ 96/102 |
| 5,808,178 | 9/1998 | Rounbehler et al. ................... 73/23.39 |

*Primary Examiner*—Michael Brock
*Attorney, Agent, or Firm*—Darby & Darby

[57] ABSTRACT

A method and apparatus for separating selected materials in a gas chromatograph. The gas mixture is introduced into a separation column of the gas chromatograph and the separation column is heated inside a chamber of the gas chromatograph to a preset temperature. The preset temperature is matched to the material to be separated and that heating is accomplished by using IR radiation.

10 Claims, 2 Drawing Sheets

METHOD FOR SEPARATING SELECTED MATERIALS IN A GAS CHROMATOGRAPH AND GAS CHROMATOGRAPH FOR CARRYING OUT THE METHOD

BACKGROUND OF THE INVENTION

The present invention relates to a method for separating selected materials in a gas chromatograph, wherein the gas mixture is introduced into a separation column of the gas chromatograph and the separation column is heated inside a chamber of the gas chromatograph to a preset temperature. The invention also provides a gas chromatograph for practicing the method. The gas chromatograph comprises an oven with a heat-resistant and insulating jacket and a closeable chamber, the chamber includes a capillary separation column which is connected to an injector and to a detector, and a heating device.

Gas chromatographs are used in measurement procedures, in particular procedures relating to the environment, for separating and analyzing the various constituent materials in gas mixtures.

For this purpose, a respective gaseous sample is introduced into a gas chromatographic separation column of a gas chromatograph together with a carrier gas and heated inside the gas chromatograph from ambient temperature to a temperature of about 300° C.

The materials evaporate in accordance with their boiling point, are transported by the carrier gas and interact with the gas chromatographic phase which is coated on the inside of the column. The individual compounds thus experience different propagation times inside the column.

This allows the separation of complex organic compounds.

The gas chromatographs consist primarily of a thermally insulated oven with an oven door and a capillary separation column located inside the oven and wound in the form of a circular coil. The separation column is connected to an injector for receiving the gas sample as well as to a detector, for example to a mass spectrometer. The detector and the mass spectrometer, respectively, are provided with a computerized evaluation and display system.

The oven further includes a heating device and a fan coupled to the heating device. A gas chromatograph of this type is known, for example, from U.S. Pat. No. 4,286,456.

The gas chromatograph is highly accurate, so that the experimental results obtained with the method are very conclusive.

Disadvantageously, however, ovens with a large internal volume have to be used, although the long separation column with a length of up to 60 m is not always required. Since the entire oven with its large internal volume and its large mass has to be heated together with the gas, an unnecessarily large amount of energy has to be supplied, while the cool-down times are also prolonged.

It is also disadvantageous that, although frequently only a few compounds are of interest, the entire gas mixture has to be separated by gas chromatography in order to prepare the column for the next analysis. Consequently, the oven and the gas mixture have to be heated to the maximum temperature so that the last compound also exits the column.

As a result, an analysis in large gas chromatographs can take up to about 30 minutes, followed by lengthy cool-down times of about 15 minutes.

The measurement cycles are very long due to the long heating and cooling times and cannot be justified if only a few compounds or a single well defined compound, rather than all compounds, have to be analyzed in the gas mixture.

Moreover, the gas chromatograph is not suited for mobile applications due to its massive construction.

SUMMARY OF THE INVENTION

It is therefore an object of the invention to develop a method and a gas chromatograph with a rapid, step-like heat-up phase and a short cool-down phase.

The object is solved by the method in that the temperature in the chamber is adapted to the material to be separated and that IR radiation is used for heating.

It is also advantageous to separate several materials by setting the predetermined temperatures to the respective material to be separated. Rapid heating produces heat-up rates of about 1000° C./min for quickly reaching the optimum temperatures.

The apparatus includes an oven having a jacket and an insulating foam is applied to the inside of the oven and the heating device comprises a heat lamp emitting IR radiation. The form and the placement of the heat lamp is matched to the form and the arrangement of the separation column and the heat lamp can be moved and driven between a heating position when the chamber is closed, and a rest position when the chamber is open.

Advantageous embodiments of the novel gas chromatograph include that the jacket of the oven comprises an insulating foam applied to the inside of the oven and the heating device comprises a heat lamp emitting IR radiation. The form and the placement of the heat lamp is matched to the form and the arrangement of the separation column and the heat lamp can be moved and driven between a heating position when the chamber is closed, and a rest position when the chamber is open. Further, the heat lamp may be a halogen lamp.

The heat lamp may be in the form of a rod-shaped heating element extending along the center axis into a cylindrically coiled separation column. The heat lamp may aslo be in the form of a flat surface radiator, which is positioned on the axis of, but outside a cylindrical coil-shaped separation column, and the diameter of the radiant energy distribution may be approximately equal to the diameter of the cylinder of the separation column. Further, the heat lamp may be in the form of a flat surface radiator, which is positioned on the axis of, but outside a disc-shaped separation column, and the diameter of the radiant energy distribution may be approximately equal to the diameter of the disc of the separation column. In addition, the heat lamp may be rigidly connected with the closing lid. Furthermore, the heat lamp may be in the form of a closing lid.

Thus, the invention eliminates the aforedescribed disadvantages of the prior art technology.

In particular, the gas chromatograph is highly efficient. Separation times are typically about 5 min and the cool-down times about 2 min. The measurement cycles thus become very short, making both the measurements cost-effective and mobile applications feasible.

Mobile applications are also facilitated by the small footprint and the light weight of the gas chromatograph, which results from the extremely small chamber volume inside the oven due to the rather short separation column with a length of only about 3 m, and the use of a light-weight heat-resistant insulating foam as oven jacket.

Since both the size and the thermal mass of the oven are small, the gas chromatograph uses very little energy.

The invention will be described hereinafter with reference to several embodiments of a gas chromatograph.

DETAILED DESCRIPTION OF THE PRESENTLY PREFERRED EMBODIMENTS

Figure 1:
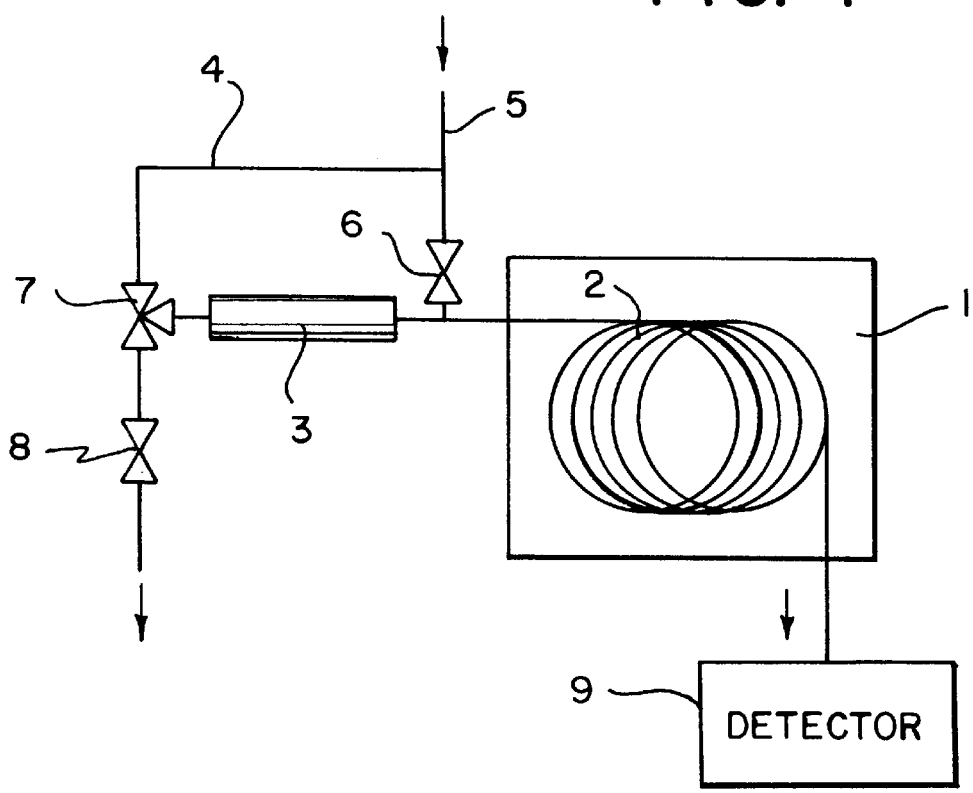
FIG. 1 a gas flow diagram of a gas chromatograph.

As illustrated in FIG. 1, a gas chromatograph includes an oven 1 and a capillary separation column 2.

The separation column 2 is connected to an injector 3 which is designed to receive a sample, wherein both sides of the injector 3 are connected to a carrier gas via a line 4 and a line 5, respectively. Valves 6, 7 and 8 are provided for switching the carrier gas flow through the injector 3, both for transporting the gas mixture to the separation column 2 and for purging the injector 3 in the reverse direction.

The separation column 2 is also connected with a detector 9 which is in turn coupled to a computerized evaluation and display system.

Figure 2A:
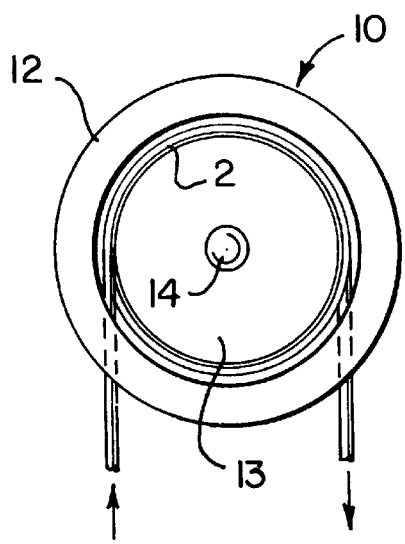
FIG. 2 a gas chromatograph with an inserted heat lamp and a cylindrical separation column, FIG. 3 a gas chromatograph with a set-top heat lamp and a cylindrical separation column, and FIG. 4 a gas chromatograph with a set-top heat lamp and a disc-shaped separation column.
Figure 2B:
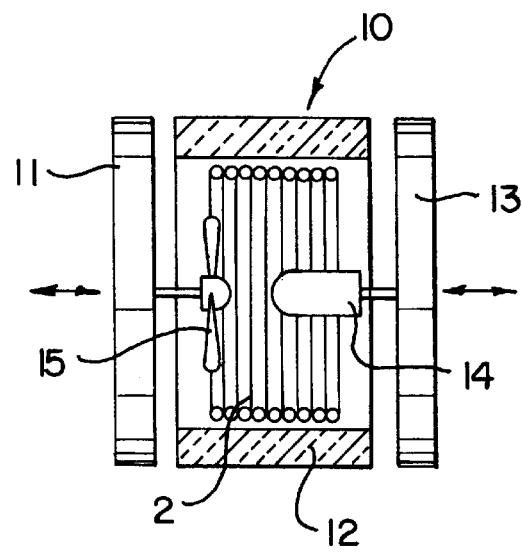
Figure 4A:
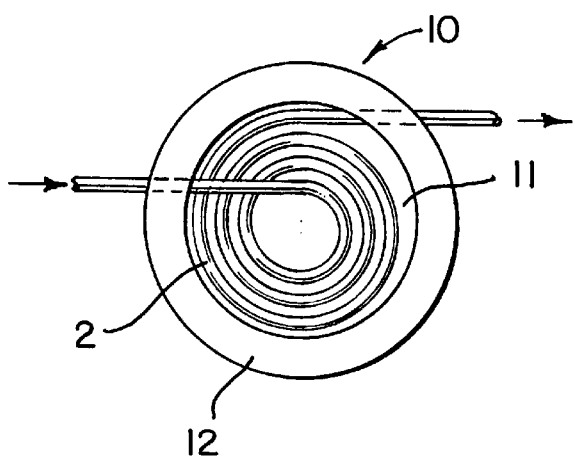
Figure 4B:
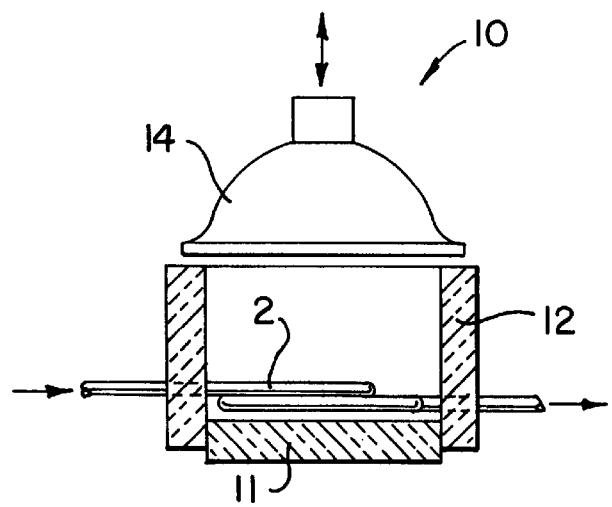

Referring now to FIGS. 2 and 4, the oven is preferably constructed as a cylindrical hollow and closeable chamber 10, which is enclosed by a bottom 11, a cylinder wall 12 and a closing lid 13. The bottom 11, the cylinder wall 12 and the closing lid 13 are made from a heat-resistant insulating foam with a high thermal insulation factor. The inner surfaces are coated with an aluminum foil or a brass foil.

At least the closing lid 13 is designed to be moveable on the cylinder axis between a closed position and an open position and is connected to a preferably pneumatic actuator. According to FIG. 2, the cool-down phase can advantageously be shortened by making both the closing lid 13 and the bottom 11 moveable.

The capillary separation column 2 is arranged in the chamber 10 in a specific coiled form in the shape of a cylinder or a disc.

When the coil is in the shape of a cylinder, the coil diameter of the separation column 2 is matched to the diameter of the chamber 10, so that the individual coil windings of the separation column 2 are proximate to and equidistant from the inner surface of the cylinder wall 12.

When the coil of the separation column 2 is in the shape of a disc, all windings are proximate to and equidistant from the bottom 11 of the chamber 10.

The oven 1 is also provided with a heat lamp 14 emitting a portion of the radiation in the IR spectral range. The heat lamp 14 is located on the inside, near the center of the closing lid 13 and is rigidly connected to the closing lid 13.

The shape of the heat lamp 14 and the position of the heat lamp 14 on the closing lid 13 is adapted to the shape and the position of the separation column 2.

As illustrated in FIG. 2, the heat lamp 14 is advantageously in the form of a rod-shaped heating element extending at least halfway into the cylindrical coil-shaped separation column 2.

Figure 3A:
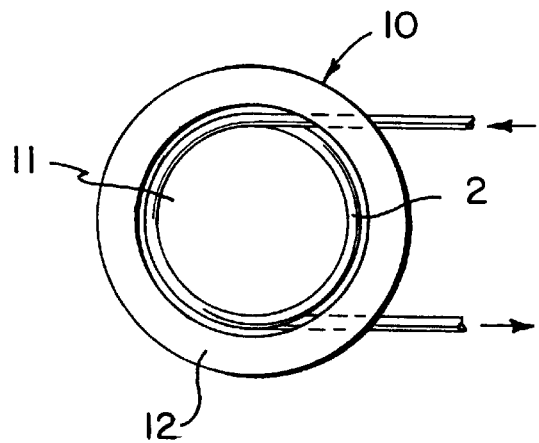
Figure 3B:
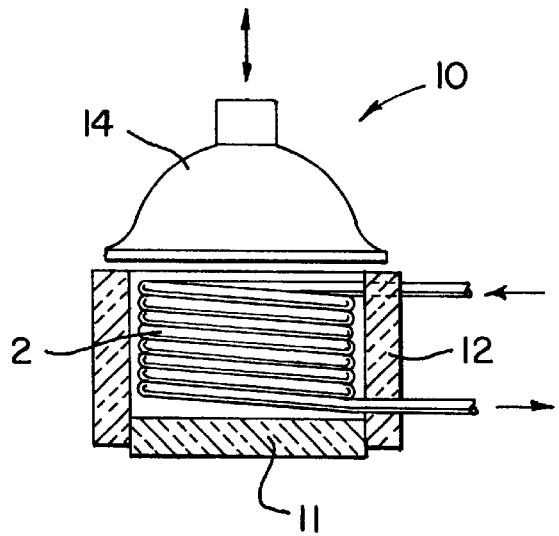

As illustrated in FIG. 3, the heat lamp 14 can advantageously also be in the form of a radiant panel, which is positioned on the axis, but outside a cylindrical coil-shaped separation column 2. The diameter of the radiant energy distribution is herein about equal to the diameter of the cylinder of the separation column 2.

As illustrated in FIG. 4, the heat lamp 14 can advantageously also be in the form of a flat surface radiator, which is positioned on the axis, but outside the disc-shaped separation column 2. The diameter of the radiant energy distribution is here about equal to the diameter of the disc of the separation column 2.

In a particular advantageous embodiment, which is also illustrated in FIGS. 3 and 4, the heat lamp 14 has the form of a lid. The heat lamp 14 is moveable between a closed position and an open position and is connected to an actuator. In the closed position, the heat lamp 14 has the dual function of both sealing and heating the chamber.

Similar to conventional chambers, the chamber 10 also includes as an option an additional fan 15 which helps smoothing any uneven temperature distribution inside the chamber 10 both during the heat-up phase and the cool-down phase in the chamber 10.

A Ni—NiCr thermocouple is located immediately adjacent to the separation column 2 for monitoring the temperature inside the chamber 10.

The heat lamp 14 is controlled by a controller.

The gas chromatograph operates as follows:

The required temperature which is specific to the material to be separated, is preset on the controller of the heat lamp 14.

The chamber 10 of the oven 1 is open. The sample is introduced into the injector 3 either manually or through a mechanical feed mechanism, then evaporated at a sufficiently high temperature and transported to the separation column 2 with the help of a carrier gas. Simultaneously, the oven is closed and the heat lamp 14 is switched on, thereby raising the temperature to the desired end temperature either continuously or in a step-like fashion in response to the desired or programmed parameters. Each individual compound then interacts with the phase of the gas chromatographic column based on the interaction of the carrier gas with the phase. The optimum separation is attained with an optimum temperature and an optimum carrier gas velocity of the column. If, for example, only one constituent component in the compound is of interest, then the optimum temperature can be reached in a single temperature step. This optimum temperature is maintained until the compound is completely separated. Thereafter, the maximum end temperature can be reached in another temperature step to remove the less volatile compounds from the separation column 2.

If several compounds are of interest, then several temperatures can be attained through respective temperature steps. It is also feasible to increase the temperature continuously, for example by following a programmed temperature profile. After the compounds have exited the separation column 2 and are detected by the detector 9, the oven 1 is opened and cooled down within a short time of about 1 to 2 minutes, so that the gas chromatograph is then ready for the next measurement.

What is claimed:

1. A method for separating selected materials in a gas chromatograph, comprising the steps of placing a shaped capillary separation column into a heat-resistant and insulated jacket of the gas chromatograph;

introducing the gas mixture into the shaped capillary separation column;

moving an IR radiation heat source, adapted to conform to the overall shape of the capillary separation column, adjacent to the capillary separation column;

providing a uniform and constant preset temperature to the separation column by utilizing the IR radiation heat source;

matching the preset temperature to the material to be separated.

2. The method according to claim 1, wherein more than one material is separated by providing a second preset constant temperature to the capillary separation column, matching the preset temperature to the second material to be separated.

3. A gas chromatograph comprising an oven including a heat-resistant jacket and a closeable chamber, in the chamber there is arranged a shaped capillary separation column connected to an injector and to a detector;

the heat-resistant jacket of the oven comprises an insulating foam applied to the inside of the oven;

a heating device including a heat lamp emitting IR radiation;

wherein the heat lamp is adapted to match the shape and arrangement of the capillary separation column; and wherein the heat lamp can be moved and driven between a heating position when the chamber is closed, and a rest position when the chamber is open.

4. A gas chromatograph comprising an oven including a heat-resistant jacket and a closeable chamber, in the chamber there is arranged a shaped capillary separation column connected to an injector and to a detector;

the heat-resistant jacket of the oven comprises an insulating foam applied to the inside of the oven;

a heating device including a heat lamp;

wherein the heat lamp is a halogen lamp and adapted to match the shape and arrangement of the capillary separation column; and wherein the heat lamp can be moved and driven between a heating position when the chamber is closed, and a rest position when the chamber is open.

5. The gas chromatograph according to claim 4, wherein the capillary separation column is shaped in form of a cylindrical coil and the heat lamp includes a rod-shaped heating element extending along a center axis of the cylindrically coiled capillary separation column.

6. The gas chromatograph according to claim 5, wherein the heat lamp is rigidly connected with a closing lid.

7. The gas chromatograph according to claim 6, wherein the oven includes a bottom, the bottom may be moved and driven.

8. The gas chromatograph according to claim 5, wherein the heat lamp is in the form of a closing lid.

9. The gas chromatograph according to claim 4, wherein the capillary separation column is shaped in form of a cylindrical coil having a diameter and the heat lamp includes a flat surface radiator and emitting radiant energy, the flat surface radiator is positioned above the cylindrically coiled capillary separation column; and wherein a diameter of radiant energy distribution is substantially equal to the diameter of the cylinder of the capillary separation column.

10. The gas chromatograph according to claim 4, wherein the capillary separation column is shaped in form of a flat spiral having a diameter and the heat lamp includes a flat surface radiator and emitting radiant energy, the flat surface radiator is positioned above the flat spiraled capillary separation column; and wherein a diameter of radiant energy distribution is substantially equal to the diameter of the disc of the capillary separation column.

* * * * *